(12) United States Patent
Leybovich

(10) Patent No.: US 6,487,910 B1
(45) Date of Patent: Dec. 3, 2002

(54) METHOD AND APPARATUS FOR QUANTITATIVE SPUTTER TARGET CLEANLINESS AND CHARACTERIZATION

(75) Inventor: Alexander Leybovich, Hilliard, OH (US)

(73) Assignee: Tosoh SMD, Inc., Grove City, OH (US)

( * ) Notice: Subject to any disclaimer, the term of this patent is extended or adjusted under 35 U.S.C. 154(b) by 0 days.

(21) Appl. No.: 09/700,268
(22) PCT Filed: Jun. 9, 1999
(86) PCT No.: PCT/US99/13066

§ 371 (c)(1),
(2), (4) Date: Nov. 9, 2000

(87) PCT Pub. No.: WO99/64854

PCT Pub. Date: Dec. 16, 1999

Related U.S. Application Data

(60) Provisional application No. 60/088,567, filed on Jun. 9, 1998.

(51) Int. Cl.[7] ................................................. G01N 29/00
(52) U.S. Cl. ........................................... 73/620; 73/600
(58) Field of Search ........................ 73/596, 599, 600, 73/602, 618, 619, 620, 627

(56) References Cited

U.S. PATENT DOCUMENTS 4,797,164 A  1/1989  Höllrigl et al.
5,160,388 A  11/1992 Legresy et al.
5,406,850 A * 4/1995 Bouchard et al. ............. 73/620
5,804,730 A * 9/1998 Pfannenstiel et al. ......... 73/622
5,887,481 A  3/1999  Leroy et al.

FOREIGN PATENT DOCUMENTS

FR  2744805  3/1998
WO  9730348  12/1996

OTHER PUBLICATIONS

Leybovich, A. et al., "Effect of Thin Film Oxide Inclusions on Aluminum Target Arcing and Particulate," *AVS 42$^{nd}$ National Symposium*, Minneapolis, MN, Oct. 16–20, 1995.

* cited by examiner

*Primary Examiner*—Richard A. Moller
(74) *Attorney, Agent, or Firm*—Biebel & French

(57) ABSTRACT

A non-destructive method for characterizing a sputter target material comprises the steps of sequentially irradiating a test sample of the sputter target material with sonic energy at a plurality of positions on a surface of the sample; detecting echoes induced by the sonic energy; discriminating texture-related back-scattering noise from the echoes to obtain modified amplitude signals; comparing the modified amplitude signals with said at least one calibration value to detect flaw data points and no-flaw data points; counting the flaw data points to determine a flaw count; counting the total flaw data points and the no-flaw data points to determine a total number of data points and calculating a cleanliness factor.

25 Claims, 5 Drawing Sheets

METHOD AND APPARATUS FOR QUANTITATIVE SPUTTER TARGET CLEANLINESS AND CHARACTERIZATION

This application claims the priority of Provisional Application No. 60/088,567, filed Jun. 9, 1998.

SUMMARY OF THE INVENTION

This invention relates to non-destructive testing methods and apparati for determining the "cleanliness," that is, degree of material internal purity, of metallic sputter target materials and, more particularly, non-destructive methods and apparati for determining cleanliness based on the sound propagation properties of the materials.

BACKGROUND OF THE INVENTION

Cathodic sputtering is widely used for depositing thin layers or films of materials from sputter targets onto desired substrates such as semiconductor wafers. Basically, a cathode assembly including a sputter target is placed together with an anode in a chamber filled with an inert gas, preferably argon. The desired substrate is positioned in the chamber near the anode with a receiving surface oriented normally to a path between the cathode assembly and the anode. A high voltage electric field is applied across the cathode assembly and the anode.

Electrons ejected from the cathode assembly ionize the inert gas. The electrical field then propels positively charged ions of the inert gas against a sputtering surface of the sputter target. Material dislodged from the sputter target by the ion bombardment traverses the chamber and deposits on the receiving surface of the substrate to form the thin layer or film.

One factor affecting the quality of the layer or film produced by a sputtering process is the "cleanliness" of the material from which the sputter target is made. The term "cleanliness" is widely used in the semiconductor industry, among others, to characterize high purity and ultra high purity materials. In common practice, "cleanliness" refers to the degree of material internal purity. Such impurities may be present, for example, as inclusions of impurity-rich phases surrounded by the sputter target material. Cleanliness is usually measured in units of particles per million ("ppm") or particles per billion ("ppb") which define a ratio between the number of contaminant atoms and the total number of atoms sampled.

Since the cleanliness of the material from which a sputter target is made affects the quality of layers of films produced using that target, it is obviously desirable to use relatively clean materials in fabricating sputter targets. This implies a need in the art for non-destructive techniques for selecting sputter target blanks of suitable cleanliness to produce high quality sputter targets. Known destructive test methods, such as glow discharge mass spectroscopy and LECO techniques, are not suitable for this purpose.

Another factor affecting the quality of the layer or film produced by a sputtering process is the presence of "flaws" in the sputter target material. As used herein, the term "flaws" refers to microscopic volumetric defects in the sputter target material, such as inclusions, pores, cavities and micro-laminations. Since flaws in a sputter target affect the quality of layers or films produced using that target, there exists a corresponding need in the art for non-destructive techniques for characterizing flaws present in sputter target materials.

FIG. 1 illustrates a prior art non-destructive ultrasonic "flaw" detection method for characterizing aluminum and aluminum alloy sputter target materials. The technique illustrated in FIG. 1 is similar to that suggested in Aluminium Pechiney PCT Application No. PCT/FR96/01959 for use in classifying aluminum or aluminum alloy blanks suitable for fabricating sputter targets based on the size and number of internal "decohesions" detected per unit volume of the blanks.

The prior art technique of FIG. 1 employed a pulse-echo method performed on a test sample 10 having a planar upper surface 12 and a parallel planar lower surface 14. In accordance with this technique, focused ultrasonic transducer 16 irradiated a sequence of positions on the upper surface 12 of the test sample 10 with a single, short-duration, high-frequency ultrasound pulse 18 having a frequency of at least 5 MHz, and preferably 10–50 MHz. The ultrasonic transducer 16 then switched to a sensing mode and detected a series of echoes 20 induced by the ultrasound pulse 18.

One factor contributing to these echoes 20 was scattering of sonic energy from the ultrasound pulse 18 by flaws 22 in the test sample 10. By comparing the amplitudes of echoes induced in the test sample 10 with the amplitudes of echoes induced in reference samples (not shown) having compositions similar to that of the test sample 10 and blind, flat-bottomed holes of fixed depth and diameter, it was possible to detect and count flaws 22 in the test sample 10.

The number of flaws detected by the technique of FIG. 1 had to be normalized in order to facilitate comparison between test samples of different size and geometry. Conventionally, the number of flaws was normalized by volume—that is, the sputter target materials were characterized in units of "flaws per cubic centimeter." The volume associated with the echoes 20 from each irradiation of the test sample 10 was determined, in part, by estimating an effective cross-section of the pulse 18 in the test sample 10.

One drawback to the technique of FIG. 1 is that a number of factors detract from the ability of the transducer 16 to detect sonic energy scattered by the flaws 22. This reduces the sensitivity of the technique.

One such factor is relative weakness of the scattered energy. A portion of the scattered energy is attenuated by the material making up the test sample 10. Furthermore, since the flaw sizes of interest, which range from approximately 0.04 mm to 0.1 mm, are significantly less than the wavelength of ultrasound in metals (for example, the wavelength of sound in aluminum for the frequency range of 10 MHz to 50 MHz is 0.6 mm to 0.12 mm, respectively), the pulse 18 has a tendency to refract around the flaws 22, which reduces the scattering intensity.

Another factor detracting from the ability of the transducer 16 to detect the sonic energy scattered by the flaws 22 is the noise generated by scattering of the pulse 18 at the boundaries between grains having different textures. In fact, the texture-related noise can be so great for high-purity aluminum having grain sizes on the order of several millimeters that small flaws within a size range of approximately 0.05 mm and less cannot be detected. Larger grain sizes reduce the signal-to-noise ratio for the sonic energy scattered by the flaws when compared to the noise induced by the grain boundaries.

Other factors affecting the sensitivity and resolution of the technique of FIG. 1 includes the pulse frequency, duration and waveform; the degree of beam focus and the focal spot size; the coupling conditions (that is, the efficiency with which the sonic energy travels from the transducer 16 to the test sample 10); and the data acquisition system parameters.

Another drawback to the technique of FIG. 1 is that the calculation of the "flaws per cubic centimeter" in the test sample 10 presupposes that only flaws 22 within a determinable cross-sectional area scatter sonic energy back toward the transducer 16. In fact, the pulse 18, due to its wave nature, does not have localized, well-determined boundaries.

The distribution of the energy of the pulse 18 within the test sample 10, under simplifying assumptions, permits one to define a corridor 30 having a determinable cross-section beneath the transducer 16 in which most of the energy should be concentrated. Nevertheless, some of the energy of the pulse 18 will propagate outside this corridor 30. As a result, the transducer may detect sonic energy scattered by relatively large flaws 22 located outside the estimated corridor 30, thereby overestimating the density of flaws 22 in the test sample 10 and underestimating their sizes. Therefore, material cleanliness characteristics become to some degree uncertain.

Thus, there remains a need in the art for non-destructive techniques for characterizing sputter target materials having greater sensitivity than methods in the prior art. There also remains a need for techniques which permit the comparison of the cleanliness of different sputter target materials in a manner which is not dependent on arbitrary volumetric estimations in the form "flow per cubic unit." One conventional imaging technique for sputter target material is C-scanning. It maps the flaws on a two-dimensional image of the material sample. Where the size of the tested object is on the order of approximately ten centimeters or greater, however, it becomes difficult to indicate the relative sizes of flaws having diameters on the order of approximately 0.04 mm to 0.1 mm to any realistic scale. When computerized imaging is used it may be impossible to indicate the relative sizes of flaws in this manner where the sizes of the flaws relative to the entire width or diameter of the sample surface are less than the relative pixel sizes of the display device.

Therefore there remains an additional need in the art for an imaging technique which does not require the display of flaws scaled relative to the surface area of the test sample.

SUMMARY OF THE INVENTION

These needs and others are addressed by a non-destructive method for characterizing a sputter target material comprising the steps of sequentially irradiating a test sample of the sputter target material with sonic energy at a plurality of positions on a surface of the sample; detecting echoes induced by the sonic energy; discriminating texture-related backscattering noise from the echoes to obtain modified amplitude signals; comparing the modified amplitude signals with said at least one calibration value to detect flaw data points and no-flaw data points (that is, data points in which flaws were detected, and were not detected, respectively); counting the flaw data points to determine a flaw count $C_F$; counting the flaw data points and the no-flaw data points to determine a total number of data points $C_{DP}$; and calculating a cleanliness factor $F_C=(C_F/C_{DP})\times10^6$.

Unlike the prior art method described earlier, the method of the present invention provides a characterization of the sputter target material which is not dependent on theoretical estimates of the cross-sectional area occupied by the sonic energy during its flight through the test sample. Since the cleanliness factor is normalized by the number of data points rather than by estimated volume, there is less risk of overestimating the number of flaws, or underestimating their sizes, than in the prior art method of FIG. 1.

Although the cleanliness factor provides a useful characterization of the sputter target material, more information can be provided by means of a histogram. More specifically, the sputter target may be characterized by defining a plurality of amplitude bands; measuring said modified amplitude signals to determine modified amplitude signal magnitudes; comparing said modified amplitude signal magnitudes with said plurality of amplitude bands to form subsets of said modified amplitude signals; counting said subsets of modified amplitude signals to determine a plurality of modified amplitude signal counts, each modified amplitude signal count of said plurality of amplitude signal counts corresponding to one of said amplitude bands of said plurality of amplitude bands; and constructing a histogram relating said modified signals counts to said plurality of amplitude bands. Since the histogram does not attempt to directly map the locations of flaws along the surface of the sputter target material, it does not suffer from the scaling problems inherent in prior art mapping techniques.

Most preferably, the test sample is compressed along one dimension, such as by rolling or forging, and then irradiated by sonic energy propagating transversely (that is, obliquely or, better yet, normally) to that dimension. This has the effect of flattening and widening any flaws in the material. The widening of the flaws, in turn, increases the intensity of the sonic energy scattered by the flaws and reduces the likelihood that the sonic energy will refract around the flaws.

These methods for characterizing sputter target materials may be used in processes for manufacturing sputter targets. As noted earlier, the cleanliness of a sputter target is one factor determining the quality of the layers or films produced by the target. By shaping only those sputter target blanks having cleanliness factors or histograms meeting certain reference criteria to form sputter targets, and rejecting blanks not meeting those criteria, one improves the likelihood that the sputter targets so manufactured will produce high quality layers or films.

Therefore, it is one object of the invention to provide non-destructive methods for characterizing sputter target materials. Other objects of the invention will be apparent from the follow description the accompanying drawings, and the appended claims.

DETAILED DESCRIPTION OF THE PREFERRED EMBODIMENTS

Figure 1:
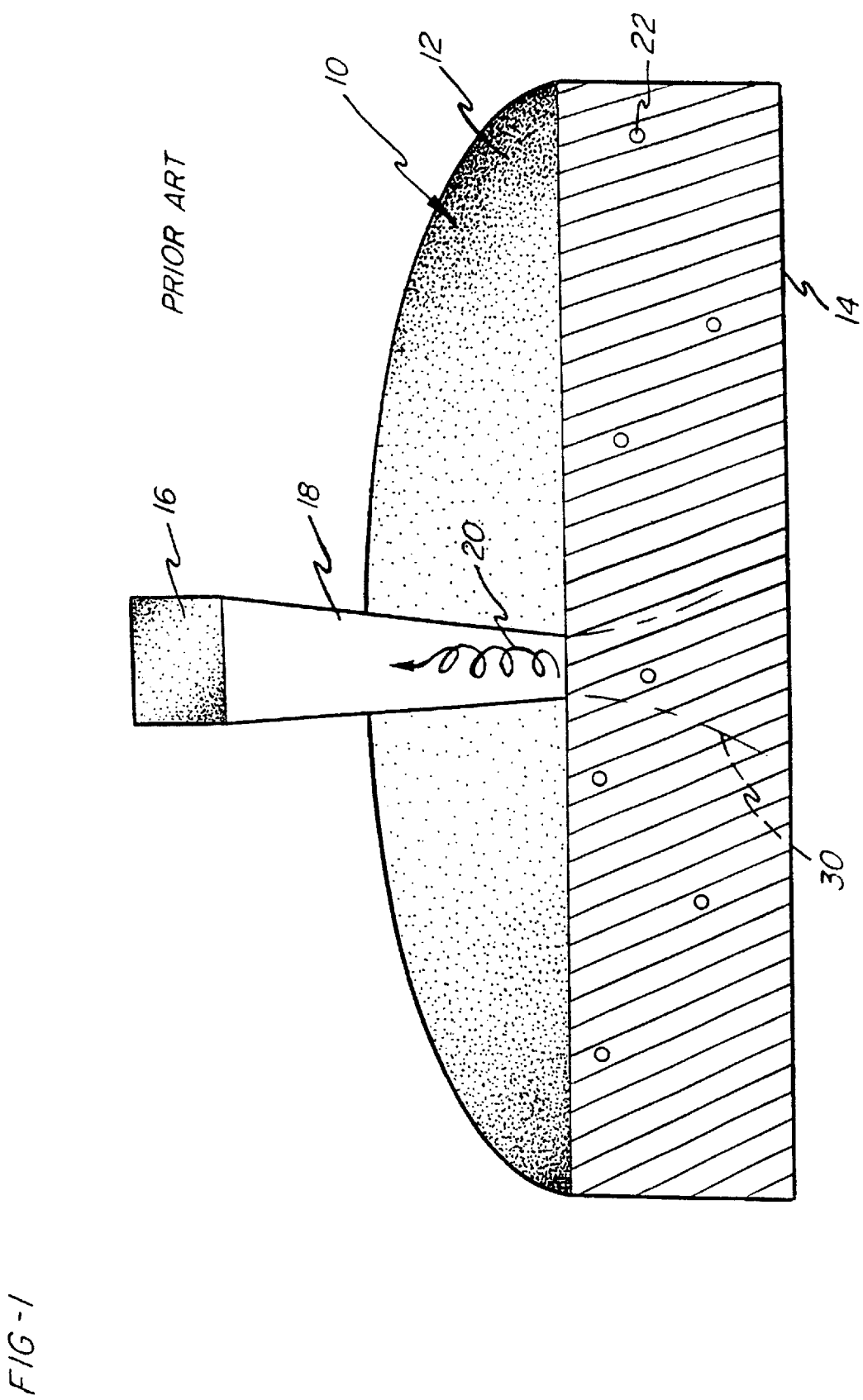
FIG. 1 is a schematic view illustrating of prior art method of ultrasonic texture analysis.
Figure 2:
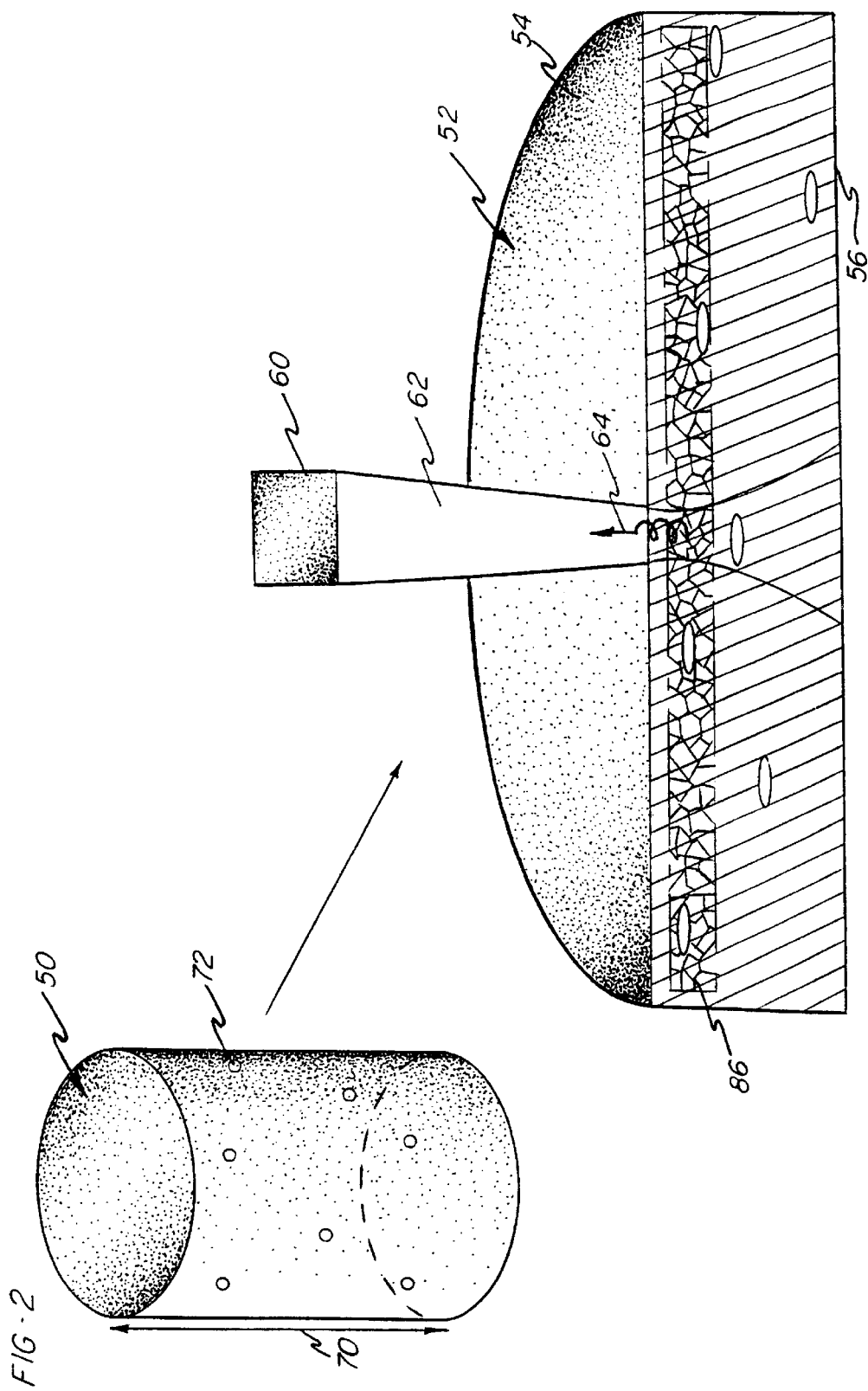
FIG. 2 is a schematic view illustrating an especially preferred method of ultrasonic cleanliness characterization in accordance with the invention.

FIG. 2 illustrates an especially preferred method for characterizing the cleanliness of sputter target material. In accordance with this method, a cylindrical sample 50 of the sputter target material (which preferably comprises metal or a metal alloy) is compressed or worked to produce a disc-shaped test sample 52 having a planar upper surface 54 and a planar lower surface 56 approximately parallel to the upper surface 54. Thereafter, a focused ultrasonic transducer 60 is positioned near the upper surface 54. The transducer 60 irradiates the upper surface 54 of the test sample 52 with a single, short-duration, megahertz frequency range ultrasonic pulse 62. The transducer 60 subsequently detects an echo 64 induced in the test sample 52 by the pulse 62. The transducer 60 converts the echo into an electrical signal (not shown), which is processed for use in characterizing the test sample 52.

More specifically, the sample 50 first is compressed along a dimension 70 to form the disc-shaped test sample 52. Preferably, the sample 50 is compressed by forging or rolling of the sample 50, followed by diamond cutting to prepare the planar surfaces 54 and 56. The reduction in the dimension 70 may be anywhere between 0% to 100%. The compression of the sample 50 flattens and widens any flaws 72, so as to increase their surface area normal to the dimension 70.

Figure 3:
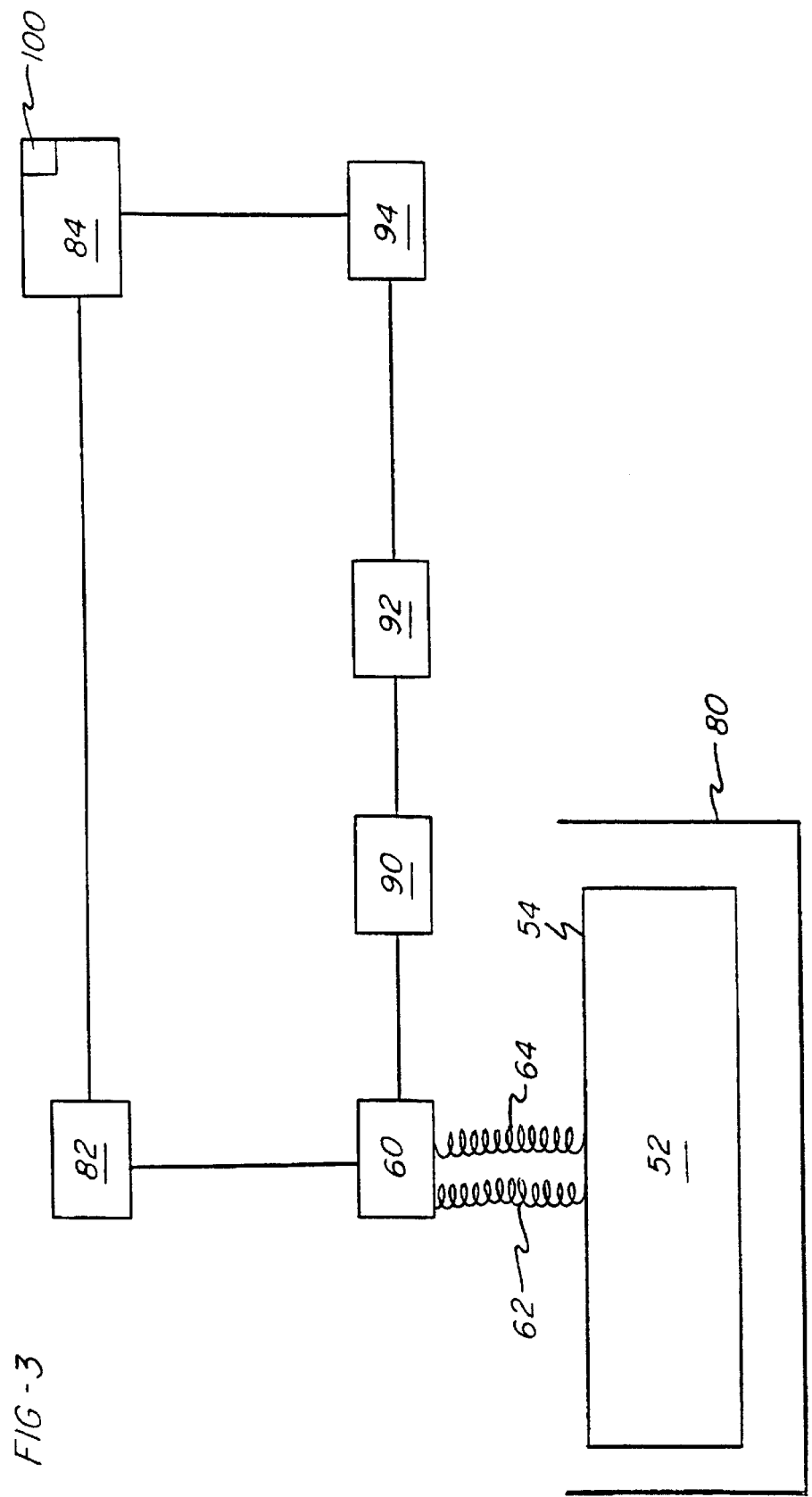
FIG. 3 is a schematic view of a test apparatus for carrying out the method of FIG. 2.

As illustrated in FIG. 3, the test sample 52 then is immersed in deionized water (not shown) in a conventional immersion tank 80. The transducer 60 is mounted on a mechanical X-Y scanner 82 in electrical communication with a controller 84 such as a PC controller. The controller 84 is programmed in a conventional manner to induce the mechanical X-Y scanning unit 82 to move the transducer 60 in a raster-like stepwise motion across the upper surface 54 of the test sample 52.

The presently preferred transducer 60 is sold by Panametrics USA under the designation V 319. This is a high resolution piezoelectric transducer having a fixed focalization distance. At a center frequency of approximately 15 MHz with a 7.2 MHz (−6 dB) bandwidth, the transducer produces a pulse 62 having a focal distance of approximately 51 mm and a focal spot 12.5 mm in diameter.

Most preferably, the upper surface 54 of the sample 52 has a width or diameter on the order of approximately 7.5 inches (approximately 19 cm). Data acquisition steps of approximately 0.8 mm in both the "x"-direction and the "y"-directions permit the detection of 0.1 mm flat bottom holes at a detection level of −6 dB without exposure area overlap. One thereby irradiates approximately 50,000–500,000 test points on the upper surface 54.

Most preferably, the transducer 60 is oriented so that the pulse 62 propagates through the deionized water (not shown) in the immersion tank 80 and strikes the test sample 52 approximately normally to the upper surface 54. Furthermore, the transducer 60 is preferably spaced from the upper surface 54 such that the pulse 62 is focused on a zone 86 (FIG. 2) of the test sample 52 between approximately 3 mm and 6.2 mm below the upper surface 54. The pulse 62 interacts with the sample 52 to induce echoes 64, which then propagate back through the deionized water (not shown) to the transducer 60 approximately 60 μsec after the pulse is sent.

To increase the signal-to-noise ratio, the zone 86 (FIG. 2) in which the pulse 62 is focused should be located near the upper surface 54. The waveform and duration of the pulse 62 should be chosen keeping in mind that very short pulses experience dispersion which smooths the pulse and makes the detection of small flaws more difficult. Therefore, it is preferred that the pulse 62 be a "Gaussian" wave packet including several cycles of oscillations.

An especially preferred echo acquisition system includes a low noise gated preamplifier 90; a low noise linear amplifier 92 with a set of calibrated attenuators with a signal (from 0.1 mm flat bottom hole)-to-noise (texture) ratio of 6 dB; and a 12-bit (2.44 mV/bit) analog-to-digital converter 94. When sufficient time has elapsed for the echoes to arrive at the transducer 60, the controller 84 switches the transducer 60 from a transmitting mode to a gated electronic receiving mode. The echoes 64 are received by the transducer 60 and converted into an RF electric amplitude signal (not shown). The amplitude signal is amplified by the preamplifier 90 and by the low noise linear amplifier 92 to produce a modified amplitude signal. The attenuators (not shown) associated with the low noise linear amplifier 92 attenuate a portion of the texture-related noise. The modified amplitude signal then is digitized by the analog-to-digital converter 94 before moving on to the controller 84. The analog-to-digital conversion is performed so as to preserve amplitude information from the analog modified amplitude signal.

Flaws of given sizes are detected by comparing the digitized modified amplitude signals obtained from the sample 52 with reference values derived from tests conducted on reference samples (not shown) having compositions similar to that of the test sample 10 and blind flat-bottomed holes of fixed depth and diameter.

The especially-preferred PC controller 84 includes a microprocessor 100 programmed to control the data acquisition process. An especially preferred software package used in connection with the data acquisition system is available from Structural Diagnostics, Inc. under the designation SDI-5311 Winscan 4.

The microprocessor 100 is also programmed to calculate the cleanliness factor characterizing the material of the samples 50, 52. More precisely, it is programmed to discriminate texture-related backscattering noise and to distinguish "flaw data points," that is, digitized modified amplitude signals received from the analog-to-digital converter 94 representing amplitudes which, after comparison with the calibrations values, indicate the presence of flaws. One especially preferred method for discriminating texture related noise is to reject echoes having amplitudes less than an echo amplitude threshold. The microprocessor 100 maintains a count of the flaw data points detected during the testing of a test sample 52 to determine a flaw count "$C_F$."

The microprocessor 100 also is programmed to distinguish "no-flaw data points," that is, digitized modified amplitude signals representing amplitudes which, after comparison with the calibration values, indicate the absence of flaws.

The microprocessor 100 also determines a total number of data points "$C_{DP}$," that is, the sum of the flaw count $C_F$ and the number of no-flaw data points. Although the total number of data points could be determined by maintaining counts of the flaw data points and the no-flaw data points, it is preferably determined by counting the total number of positions "$C_1$" along the upper surface 54 at which the test sample 52 is irradiated by the transducer 60 and subtracting the number of digitized RF signals "$C_N$" which the data acquisition circuitry was unable due to noise or other causes, to identify as either flaw data points or no-flaw data points. (Alternatively, the "noise count" $C_N$ may be described as the number of positions along the upper surface 54 at which neither a flaw data point nor a no-flaw data point is detected.)

Having determined the flaw count $C_F$ and the total number of data points $C_{DP}$, the microprocessor is programmed to calculate the cleanliness factor $F_C=(C_F/C_{DP})\times 10^6$ to characterize the material comprising the samples 50, 52. Unlike the prior art "flaws per cubic centimeter," the magnitude of the cleanliness factor is not dependent on any estimate of pulse cross-sectional area Since the cleanliness factor is normalized by the dimensionless coefficient $C_{DP} \times 10^{-6}$ rather than by volume, it is more closely related to ppm and ppb units than are units of "flaws per cubic centimeter."

The preparation of a suitable program for determining the cleanliness factor in accordance with the invention as disclosed herein is within the ordinary skill in the art and requires no undue experimentation.

Another way in which to characterize the material comprising the samples 50, 52 is by determining the size distribution of flaws in the test sample 52. More specifically, one may characterize the cleanliness of the sample 52 by defining amplitude bands or ranges; comparing the amplitudes represented by the digitized modified amplitude signal magnitudes with the amplitude bands to form subsets of the modified amplitude signals; counting these subsets of modified amplitude signals to determine a modified amplitude signal counts for each amplitude band; and constructing a histogram relating the modified signal counts to said plurality of amplitude bands. Since the amplitudes represented by the digitized modified amplitude signals are related to the sizes of flaws detected in the sample 52, the histogram provides an indication of the flaw size distribution in the sample 52.

Figure 4:
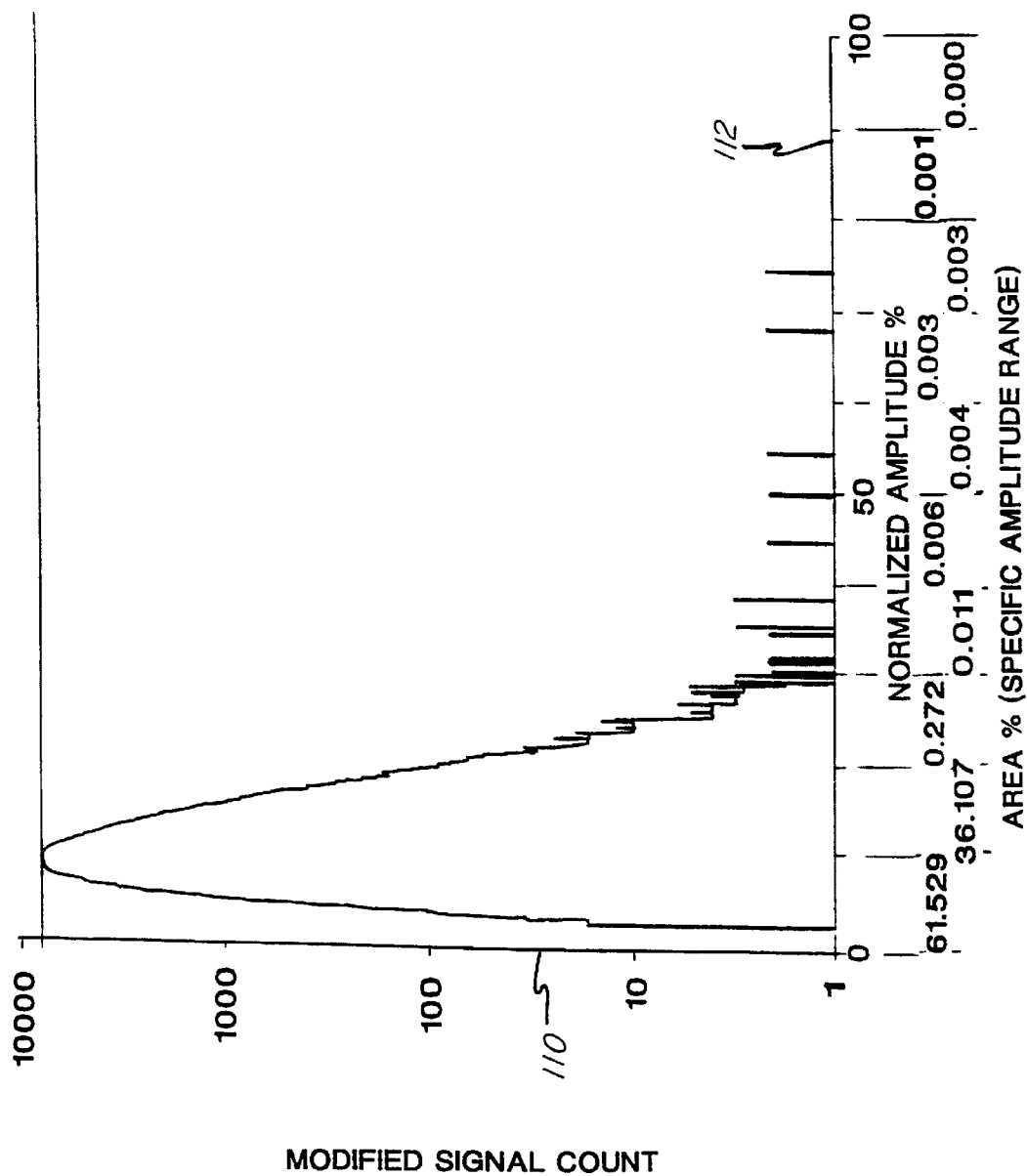
FIG. 4 is a histogram characterizing a relatively "clean" ("cleanliness factor" 183 flaw counts per million) Al-0.5 wt % Cu material in accordance with an especially preferred form of the invention.
Figure 5:
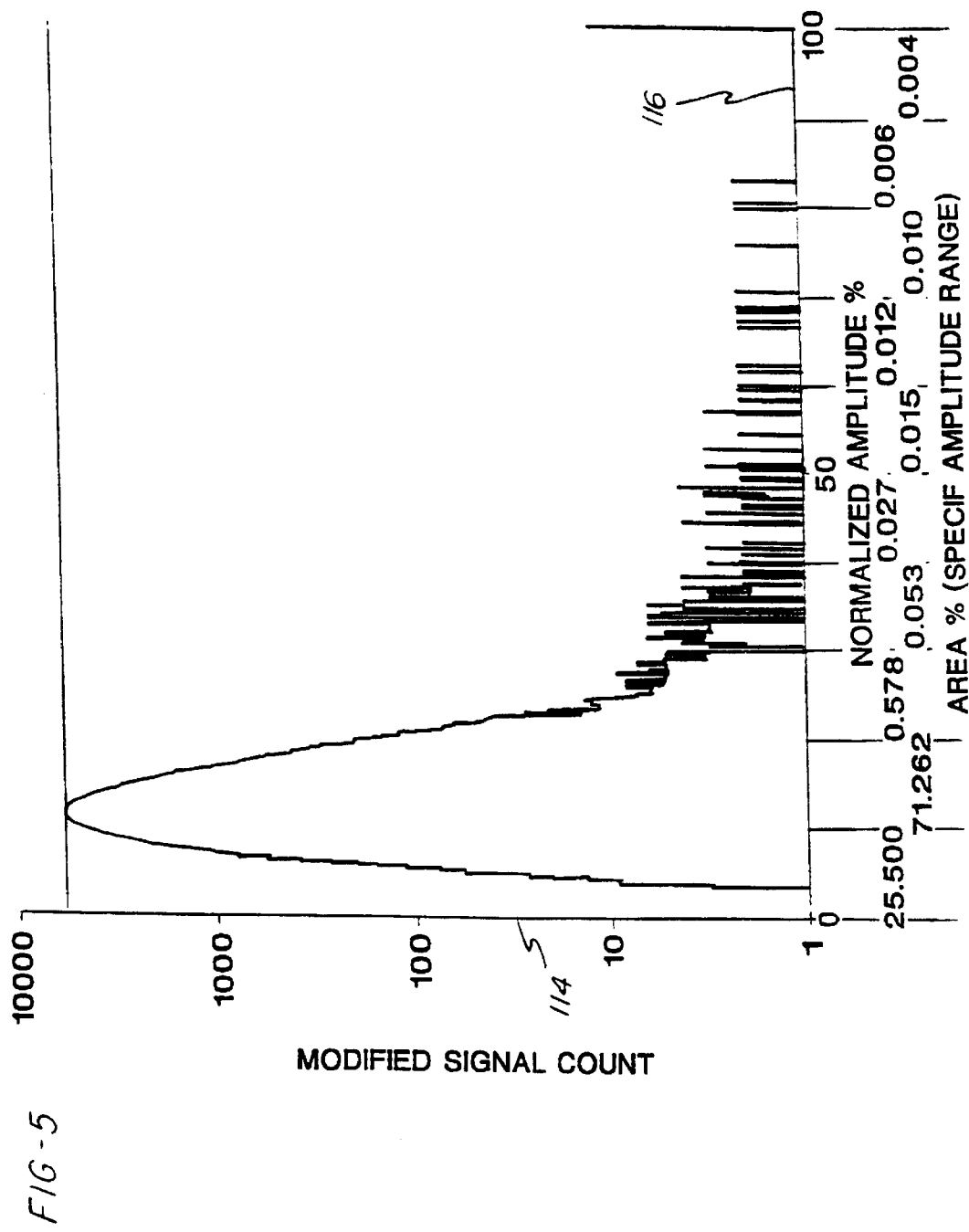
FIG. 5 is a histogram characterizing a less "clean" ("cleanliness factor" 1,714 flaw counts per million) Al-0.5 wt % Cu material in accordance with the especially preferred form of the invention.

Turning now to FIGS. 4 and 5, there may be seen histograms characterizing two Al-0.5 wt % Cu alloy sputter target materials having orthorhombic textures and grain sizes in the range of 0.08 mm to 0.12 mm. The material of FIG. 4 was "cleaner" than that of FIG. 5; the material of FIG. 4 had a cleanliness factor of 183, while the material of FIG. 5 had a cleanliness factor signal of 1,714. The zone of flaw monitoring was located within a gate of 1 microsecond duration with a gate delay of 0.9 microseconds.

The abscissa 100 of the histogram of FIG. 4 represents amplitude normalized as a percentage of the echo amplitude induced in a reference sample having a 0.1 mm blind, flat-bottomed hole. The ordinate 102 in FIG. 4 represents the modified signal counts for each amplitude, expressed on a logarithmic scale. The echo amplitude threshold for the flaw counting was set to 48% since, as established experimentally, the texture-related echo amplitude did not exceed 45% for all aluminum alloys tested. The abscissa 104 and ordinate 106 of the histogram of FIG. 5 were scaled similarly.

The histograms of FIGS. 4 and 5 represent an improvement over prior art imaging techniques in that the distribution of flaw sizes may be represented without having to represent flaw sizes relative to the surface area of the test sample (not shown).

The preparation of a suitable program for plotting histograms such as those shown in FIGS. 4 and 5 in accordance with the invention as disclosed herein is within the ordinary skill in the art and requires no undue experimentation.

Either the cleanliness factor or histograms such as those shown in FIGS. 4 and 5 may be used in a process for manufacturing sputter targets. As noted earlier, the cleanliness of a sputter target is one factor determining the quality of the layers or films produced by the target. By shaping only those sputter target blanks having cleanliness factors less than reference cleanliness factors, or having histograms with selected columns or areas less than reference values, to form sputter targets, and rejecting blanks not meeting those criteria, one improves the likelihood that the sputter targets so manufactured will produce high quality layers or films.

While the method herein described, and the form of apparatus for carrying this method into effect, constitutes a preferred embodiment of this invention, it is to be understood that the invention is not limited to this precise method and form of apparatus, and that changes may be made in either without departing from the scope of the invention, which is defined in the appended claims.

What is claimed is:

1. A method for characterizing sputter target material comprising the steps of:
    (a) sequentially irradiating a test sample of the sputter target material with sonic energy at a plurality of positions on a surface of said sample;
    (b) detecting echoes induced by said sonic energy;
    (c) comparing amplitudes of said echoes with at least one calibration value to detect flaw data points and no-flaw data points;
    (d) counting said flaw data points to determine a flaw count $C_F$;
    (e) determining a total number of data points $C_{DP}$ equal to a sum of said flaw count and a count of said no-flaw data points; and
    (f) calculating a cleanliness factor $F_C = (C_F/C_{DP}) \times 10^6$.

2. The method as recited in claim 1 wherein said sputter target material comprises metal.

3. The method as recited in claim 1 including the additional steps of forming a blind, flat-bottomed hole in a reference sample having a composition substantially identical to said sputter target material; irradiating said reference sample with a sonic pulse propagating substantially parallel to a length of said hole; and detecting echoes induced by said sonic pulse to determine said at least one calibration value.

4. The method as recited in claim 1 wherein said step (a) comprises immersing said target in a fluid and generating said sonic energy in said fluid proximate said sample.

5. The method as recited in claim 1 wherein said surface is substantially planar and wherein step (a) comprises irradiating said sample with sonic energy propagating substantially normally to said surface.

6. The method as recited in claim 1 wherein said step (c) includes discriminating texture-related backscattering noise from said echoes to obtain modified amplitude signals and comparing said modified amplitude signals with said at least one calibration value to detect said flaw data points and said no-flaw data points.

7. The method as recited in claim 6 wherein said step (e) includes counting said plurality of positions to determine a total number of irradiations $C_1$; counting each of said plurality of positions at which neither a flaw data point nor a no-flaw data point is detected to determine a noise count $C_N$; and calculating said total number of data points $C_{DP} = C_1 - C_N$.

8. A method for characterizing sputter target material comprising the steps of:
    (a) compressing said test sample along one dimension of said sample;
    (b) sequentially irradiating a test sample of the sputter target material with sonic energy propagating transversely to said dimension at a plurality of positions on a surface of said sample;
    (c) detecting echoes induced by said sonic energy;
    (d) comparing amplitudes of said echoes with at least one calibration value to detect flaw data points and no-flaw data points;
    (e) counting said flaw data points to determine a flaw count $C_F$, (f) determining a total number of data points $C_{DP}$ equal to a sum of said flaw count and a count of said no-flaw data points; and (g) calculating a cleanliness factor $F_C=(C_F/C_{DP})\times 10^6$.

9. The method as recited in claim 8 wherein said sputter target material comprises metal.

10. The method as recited in claim 8 wherein said step (a) includes rolling said test sample.

11. The method as recited in claim 8 wherein said step (a) includes forging said test sample.

12. The method as recited in claim 8 including the additional steps of forming a blind, flat-bottomed hole in a reference sample having a composition substantially identical to said sputter target material; irradiating said reference sample with a sonic pulse propagating substantially parallel to a length of said hole; and detecting echoes induced by said sonic pulse to determine said at least one calibration value.

13. The method as recited in claim 8 wherein said step (b) comprises immersing said target in a fluid and generating said sonic energy in said fluid proximate said sample.

14. The method as recited in claim 8 wherein said surface is substantially planar and wherein step (b) comprises irradiating said sample with sonic energy propagating substantially normally to said surface.

15. The method as recited in claim 8 wherein said step (d) includes discriminating texture-related backscattering noise from said echoes to obtain modified amplitude signals and comparing said modified amplitude signals with said at least one calibration value to detect said flaw data points and said no-flaw data points.

16. The method as recited in claim 15 wherein said step (f) includes counting said plurality of positions to determine a total number of irradiations $C_1$; counting each of said plurality of positions at which neither a flaw data point nor a no-flaw data point is detected to determine a noise count $C_N$; and calculating said total number of data points $C_{DP}=C_1-C_N$.

17. A method for manufacturing sputter targets comprising the steps of:

(a) sequentially irradiating a sputter target blank with sonic energy at a plurality of positions on a surface of said sputter target blank;

(b) detecting echoes induced by said sonic energy;

(c) comparing amplitudes of said echoes with at least one calibration value to detect flaw data points and no-flaw data points;

(d) counting said flaw data points to determine a flaw count $C_F$;

(e) determining a total number of data points $C_{DP}$ equal to a sum of said flaw count and a count of said no-flaw data points; and (f) calculating a cleanliness factor $F_C=(C_F/C_{DP})\times 10^6$;

(g) shaping said sputter target blank to form a sputter target when said cleanliness factor is less than said reference cleanliness factor; and (h) rejecting said sputter target blank when said cleanliness factor is greater than said reference cleanliness factor.

18. The method as recited in claim 17 wherein said sputter target blank comprises metal.

19. The method as recited in claim 17 including the additional step of compressing said sputter target blank along one dimension of said sputter target blank and wherein said step (a) includes irradiating said sputter target blank with sonic energy propagating transversely to said dimension.

20. The method as recited in claim 19 wherein said additional step of compressing said sputter target blank includes rolling said sputter target blank.

21. The method as recited in claim 19 wherein said additional step of compressing said sputter target blank includes forging said test sputter target blank.

22. The method as recited in claim 17 including the additional steps of forming a blind, flat-bottomed hole in a reference sample having a composition substantially identical to said sputter target material; irradiating said reference sample with a sonic pulse propagating substantially parallel to a length of said hole; and detecting echoes induced by said sonic pulse to determine said at least one calibration value.

23. The method as recited in claim 17 wherein said step (c) includes discriminating texture-related backscattering noise from said echoes to obtain modified amplitude signals and comparing said modified amplitude signals with said at least one calibration value to detect said flaw data points and said no-flaw data points.

24. The method as recited in claim 17 wherein said step (e) includes counting said plurality of positions to determine a total number of irradiations $C_1$; counting each of said plurality of positions at which neither a flaw data point nor a no-flaw data point is detected to determine a noise count $C_N$; and calculating said total number of data points $C_{DP}=C_1-C_N$.

25. Apparatus for characterizing sputter target material comprising:

a transducer for sequentially irradiating a test sample of the sputter target material with sonic energy and detecting echoes induced by said sonic energy;

a scanner mounting said transducer for moving said transducer along a surface of the test sample; and a controller programmed to compare amplitudes of said echoes with at least one calibration value to detect flaw data points and no-flaw data points, to count said flaw data points to determine a flaw count $C_F$, to determine a total number of data points $C_{DP}$; and to calculate a cleanliness factor $F_C=(C_F/C_{DP})\times 10^6$.

* * * * *